United States Patent [19]

Mauvernay et al.

[11] 4,008,329
[45] Feb. 15, 1977

[54] SUBSTITUTED CYCLOHEXANES, PHARMACEUTICAL COMPOSITIONS CONTAINING THEM AND METHOD OF TREATMENT INVOLVING THEIR USE

[75] Inventors: Roland-Yves Mauvernay, Riom; Norbert Busch, Manzat; Jacques Moleyre, Riom; Jacques Simons, Chamalieres; Andre' Monteil, Chatel-Guyon, all of France

[73] Assignee: Societe Ananymedite: Centre European de Recherches Mauvernay (C.E.R.M.), Riom, France

[22] Filed: Aug. 4, 1975

[21] Appl. No.: 601,864

[30] Foreign Application Priority Data

Aug. 5, 1974 France .......................... 74.27168

[52] U.S. Cl. .......................... 424/330; 260/348 C; 260/570.5 CA; 260/612 D
[51] Int. Cl.² .......................................... A01N 9/20
[58] Field of Search .......... 260/570.5 CA; 424/316, 424/330

[56] References Cited

UNITED STATES PATENTS

| 3,314,896 | 4/1967 | Tinsley et al. ............. 260/348.6 X |
| 3,609,197 | 9/1971 | Leffingsell et al. ............. 260/631.5 |
| 3,836,534 | 9/1974 | Drukker et al. ..................... 260/268 |

FOREIGN PATENTS OR APPLICATIONS

662,591 12/1951 United Kingdom ............ 258/570.5

*Primary Examiner*—Robert V. Hines
*Attorney, Agent, or Firm*—DeLio and Montgomery

[57] ABSTRACT

Novel compounds, certain 3-aryloxy-2-hydroxy-cyclohexyl-amines, having valuable pharmacological properties e.g. antidepressant activity are described together with a process for their preparation, pharmaceutical compositions thereof and a method of treatment involving their use.

13 Claims, No Drawings

SUBSTITUTED CYCLOHEXANES, PHARMACEUTICAL COMPOSITIONS CONTAINING THEM AND METHOD OF TREATMENT INVOLVING THEIR USE

The present invention relates to novel substituted cyclohexanes, a method for their preparation, pharmaceutical compositions containing them and a method of treatment involving their use.

3-Aryloxy-2-hydroxy-propylamines of the formula:

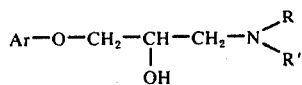

in which R and R' can have various values, are described in Belgian Pat. No. 669401, Dutch Pat. Nos. 6608099 and 6409883 and U.S. Pat. No. 3309406 and compounds of this type are known as adrenergic $\beta$-blocking agents.

One of our objects in making the present invention was to provide novel compounds having valuable pharmacological properties and pharmaceutical compositions thereof. A further object was to provide a method of treatment using the compounds and compositions. A still further object was to devise a particularly satisfactory process for making the compounds.

Compounds according to the present invention are of the general formula:

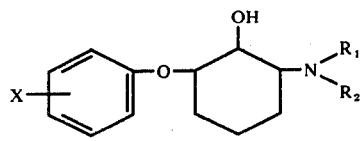

in which X represents a halogen atom, preferably chlorine or fluorine, at the 3- or 4- position of the phenoxy group or a —$CF_3$ group at the 3- position of the phenoxy group and $R_1$ and $R_2$ both represent hydrogen, both represent lower alkyl or one represents hydrogen and the other represents an isopropyl, sec-butyl, n-butyl, isoamyl, or 2-phenyl-isopropyl group. Where both $R_1$ and $R_2$ represent lower alkyl, the alkyl groups may be the same or different; normally each alkyl group will contain from one to 6 carbon atoms, preferably one to 4 carbon atoms. Also, within the scope of the invention are pharmaceutically acceptable acid addition salts of compounds of the above general formula e.g. salts with inorganic acids such as hydrochloric acid and organic acids. The salts can be made from the free bases by conventional means and may likewise be converted to the free bases.

We have found that, surprisingly, the compounds of the present invention, unlike 3-aryloxy-2-hydroxy-propylamines, do not possess any significant adrenergic $\beta$-blocking activity but that, in contrast, they possess valuable antidepressant activity and other useful pharmacological properties.

The process according to the invention for making the novel compounds can be represented by the following scheme in which X, $R_1$ and $R_2$ are as defined above:

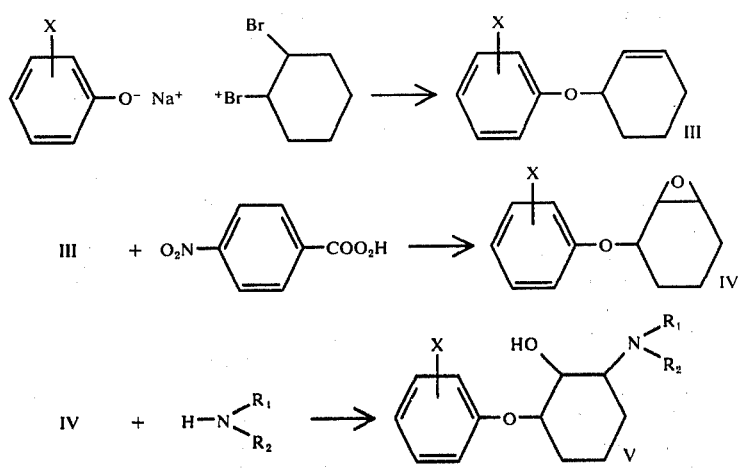

Thus, the first stage of the process is the condensation of 1,2-dibromocyclohexane with a sodium or other alkali metal phenate to give a phenoxy cyclohexene-2. This stage is conveniently carried out in the presence of ethanol or other lower alkanol and the method is analogous to that described by GOGEK and Colleagues [Can. J. Chem. 29. 938 (1951)] for the preparation of 1-methoxy-cyclohexene-2. In the next stage, the product is epoxidised to give the corresponding 1-phenoxy-2,3-epoxy-cyclohexane, conveniently by use of a per-acid, e.g. an organic per-acid such as p-nitroperbenzoic acid in an inert solvent such as chloroform. Finally, the epoxy compound is condensed with ammonia or an appropriate primary or secondary amine, this step desirably being carried out in ethanol or other lower alkanol.

Preferred phenate reactants for the first stage are sodium 3-chloro-phenate, sodium 4-chloro-phenate, sodium phenate, and sodium 4-fluoro-phenate. Preferred amino reactants for the last stage are ammonia, sec-butylamine, iso-amylamine, n-butylamine and 2-phenyl-isopropylamine.

The pharmacological activity of the compounds according to the invention, which behave like tricyclic antidepressants by inhibiting the capturing of serotonin (by abbreviation 5HT) at the central position, has been demonstrated by the test using H75/12 (3-hydroxy-4-methyl $\alpha$-ethyltyramine hydrochloride), which leads, in mice to a depletion of catecholamine and of serotonin, in accordance with the effects described by Carlson A., Corrodi H., Fuke K., and Hokfelt T. (European J. Pharmacol 5 357–366 (1969) ).

In the experiments carried out, the H 75/12 was administered on two occasions with an interval of two hours between them, in a proportion of 100mg/kg by intraperitoneal method.

In Table I hereafter, the first figure represents the first dose in mg/kg by intraperitoneal method, of the product according to the invention, administered thirty minutes before the injection of H75/12, and the second figure represents the percentage of inhibition of the depletion of serotonin in relation to a reference batch which has received only H75/12. The compounds signified by Compound Nos. 1–14 in Table 1 are indicated hereafter in Table II.

Table I also shows, as complementary pharmacological information, the results of the supramaximal electrical shock test carried out on mice by means of corneal electrodes (square wave current of constant intensity: 50mA, 50Hz, 10 ms for 0.2 seconds); the values shown in the table represent the ED 50 (for oral administration) for the products of the invention, that is to say the doses which protect 50% of the animals from tonic tension.

Finally, Table I also shows the activity of the products of the invention in regard to some cardiac parameters: the blood pressure, the systolic frequency and the right ventricular inotropism.

Experiments were carried out on chloralised dogs: these consisted of measuring, as a percentage relative to the weight of reference animals, the modifications caused by the products of the invention, administered in a proportion of 5mg/kg by intravenous route, on hypotension (H), tachycardia (T), and positive inotropism (I$^+$) induced by isoprenaline previously administered in a proportion of 0.5µg/kg by intravenous route.

The values obtained with propranolol are indicated for reference purposes to demonstrate the absence or low intensity of the adrenergic β-blocking effect of the products according to this invention.

The LD50 of all the compounds are not shown in this table but it may be stated that the LD50 (for oral administration) for mice, of compound No. 1 is 588 mg/kg and that the LD 50 values for the other compounds are of the same order of magnitude.

ing from a condition of depression an effective amount of a compound according to the invention. The method is particularly valuable for humans but is also applicable to animals, especially mammals. For humans a suitable daily dose is generally from 50 to 300 mg and the preferred manner of administration is orally. The compounds may be administered in the form of conventionally formulated pharmaceutical compositions and a pharmaceutical composition according to the invention comprises a compound according to the invention together with a pharmaceutically acceptable diluent or carrier. The diluent or carrier may be conventional. The composition may be in unit dosage form such as tablets and capsules and preferred compositions contain from 50 to 100 mg of the active compound per unit dose. The following is an example of a tablet formulation:

| | |
|---|---|
| Compound No. 1 | 50 mg |
| Lactose | 108 mg |
| Avicel (microcrystalline cellulose) | 60 mg |
| Starch | 31 mg |
| Polyvinylpyrrolidone | 4 mg |
| Talc | 5 mg |
| Stearate | 2 mg |

Compounds according to the invention and the process for their preparation are illustrated by the following Example.

EXAMPLE 2-hydroxy-3-(3'-chloro-phenoxy)-N-isopropyl-cyclohexylamine 1. 1-(3+-chloro-phenoxy)-cyclohexene-2

To a solution of sodium ethoxide in ethanol, prepared with 138g of Na (6gram-atoms) and 1800ml of ethanol, there are slowly added 257g (2 moles) of 3-chloro-phenol, and then 484g (2 moles) of dibromocyclohexane are added, drop by drop with thorough agitation and with the temperature maintained at about 35° C.

This is followed by refluxing for a further 7 hours, cooling, filtering of the sodium bromide and expelling of the solvent under vacuum. The residue is taken up in

TABLE I

| COMPOUND No. | TEST AT H 75/12 | | ED 50 ELECTROSHOCK in mg/kg P.O. | CARDIOVASCULAR PARAMETERS | | |
|---|---|---|---|---|---|---|
| | Dose in mg/kg I.P. | Percentage of inhibition of depletion on 5 HT | | H | T | I$^+$ |
| 1 | 40 | +99 | 100 | 0 | 0 | 0 |
| 2 | 40 | +42 | 300 | +30 | −20 | −15 |
| 3 | 10 | +30 | 100 | 0 | 0 | 0 |
| 4 | 10 | +59 | 25 | 0 | 0 | 0 |
| 5 | 40 | +26 | / | 0 | −39 | +25 |
| 6 | 40 | +74 | <100 | −18 | −20 | 0 |
| 7 | 30 | +93 | 30 | −50 | −50 | −38 |
| 8 | 40 | +59 | 200 | 0 | −10 | −27 |
| 9 | 20 | +18 | 250 | +30 | +9 | +25 |
| 10 | 30 | +92 | 80 | 0 | 0 | 0 |
| 11 | 40 | +118 | / | 0 | −60 | −10 |
| 12 | 20 | +120 | <50 | +35 | −35 | 0 |
| 13 | 40 | +62 | / | 0 | 0 | 0 |
| 14 | 40 | +38 | / | 0 | 0 | 0 |
| PROPRANOLOL | / | / | / | −100 | −92 | −98 |

The above results indicate the usefullness of the compounds according to the invention as antidepressant-psychotonics. A method of treatment according to the invention comprises administering to a subject sufferether. The ether phase is washed in a 10% solution of NaOh to remove the unreacted phenol, and then dried on anhydrous Na$_2$SO$_4$.

200 g are obtained, by distillation, of a product as follows:

Boiling point (1mm) = 87° C $n_D^{20}$ = 1.5581

Purity, by vapour phase chromatography: 98–99%

2. 1-(3'-chloro-phenoxy)-2,3-epoxy-cyclohexane 200g of the product of the first stage are added, drop by drop to 1500 ml of chloroform and 200g of 4-nitroperbenzoic acid. Cooling is carried out to keep the temperature in the vicinity of 20° C during the addition. Agitation is carried out for 5 hours at ambient temperature. After filtering, the chloroformic solution is washed with a 5% solution of $Na_2CO_3$, then with water. Drying is carried out on $Na_2SO_4$ to give, by distillation, 160g of product having the properties: Boiling Point$_{(1mm)}$ = 110°–111° C and $n_D^{20}$ = 1.5532, the purity by vapour phase chromatography being 98%.

3. 2-hydroxy-3-(3'-chloro-phenoxy)-N-isopropyl-cyclohexylamine 160g of the epoxy of the second stage, 400ml of ethanol and 175 g of isopropylamine are heated to 80° C in a closed vessel for 8 hours.

After the excess isopropylamine and ethanol have been expelled under vacuum, the residue is distilled to obtain 105g of the product having the properties: Boiling point$_{(1mm)}$ = 148° C, $n_D^{20}$ = 1,5410, purity by vapour phase chromatography: 98%.

The hydrochloride is prepared in the usual manner by dissolving the base in anhydrous ether and by adding the equivalent quantity of anhydrous HCl dissolved in absolute ethanol.

After drying to constant weight, 111g of hydrochloride having a fusion point of 188° C, and a molecular weight of 320.27 are obtained.

Analyses:

|  | C | N | N | HCl |
|---|---|---|---|---|
| Calculated: | 56.25% | 7.25% | 4.35% | 11.07% |
| Found: | 56.31% | 7.40% | 4.37% | 11.15% |

Further compounds according to the invention, and their hydrochlorides, were prepared by a procedure analogous to that described above but using the appropriate reactants and details of these compounds together with those for the compound described above (compound No. 1) are given in the following Table.

TABLE II

Compounds having the formula:

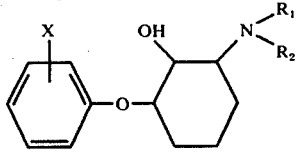

| Compound No. | —X | $R_1$ | $R_2$ | M.p. ° C Hydrochloride | Molecular weight | C % Calculated Found | H % | N % |
|---|---|---|---|---|---|---|---|---|
| 1 | 3-Cl | —H | —CH(CH₃)CH₃ | 188 | 320,27 | 56,25 / 56,31 | 7,23 / 7,40 | 4,35 / 4,37 |
| 2 | 4-Cl | —H | —CH(CH₃)CH₃ | 193 | 320,27 | 56,25 / 56,48 | 7,23 / 7,49 | 4,35 / 4,38 |
| 3 | 4-Cl | —H | —CH₂—CH(CH₃)CH₃ | 189 | 334,29 | 57,48 / 57,68 | 7,53 / 7,36 | 4,19 / 4,17 |
| 4 | 4-Cl | —H | CH₂—CH₂—CH(CH₃)CH₃ | 203 | 348,32 | 58,62 / 58,72 | 7,81 / 7,58 | 4,02 / 3,97 |
| 5 | —H | —H | —CH(CH₃)CH₃ | 205 | 285,82 | 63,03 / 62,98 | 8,46 / 8,30 | 4,90 / 4,87 |
| 6 | 3-CF₃ | —H | —CH(CH₃)CH₃ | 203 | 353,82 | 54,31 / 54,59 | 6,55 / 6,81 | 3,96 / 4,07 |
| 7 | 3-CF₃ | —H | CH₂—CH₂—CH(CH₃)CH₃ | 197 | 381,87 | 56,61 / 56,30 | 7,13 / 7,22 | 3,67 / 3,75 |
| 8 | 4-F | —H | —CH(CH₃)CH₃ | 174 | 303,81 | 59,30 / 59,55 | 7,63 / 7,52 | 4,61 / 4,58 |
| 9 | 4-F | —CH₃ | —CH₃ | 179 | 289,78 | 58,02 / 57,90 | 7,30 / 7,34 | 4,83 / 4,84 |
| 10 | 3-Cl | —H | n—C₄H₉ | 214 | 334,29 | 57,48 / 57,58 | 7,53 / 7,64 | 4,19 / 4,15 |
| 11 | —H | —H | —CH(CH₃)—CH₂—C₆H₅ | 198 | 361,92 | 69,69 / 69,67 | 7,80 / 7,84 | 3,87 / 3,89 |

TABLE II-continued

Compounds having the formula:

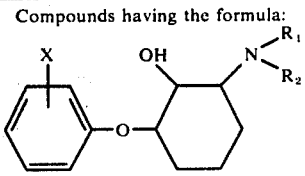

| Compound No. | —X | $R_1$ | $R_2$ | M.p. °C Hydrochloride | Molecular weight | C % Calculated Found | H % | N % |
|---|---|---|---|---|---|---|---|---|
| 12 | 4-F | —H | —CH—CH$_2$—⟨phenyl⟩ / CH$_3$ | 229 | 379,91 | 66,39 / 66,55 | 7,16 / 7,05 | 3,68 / 3,70 |
| 13 | 4-Cl | —H | —H | 272 | 278,19 | 51,81 / 51,56 | 6,16 / 6,20 | 5,03 / 4,98 |
| 14 | 4-Cl | —CH$_3$ | —CH$_3$ | 227 | 306,24 | 54,99 / 54,74 | 6,92 / 7,18 | 4,58 / 4,59 |

We claim:

1. Compounds of the general formula:

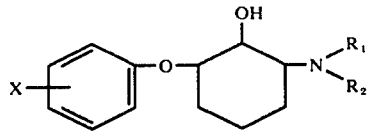

in which X represents a halogen atom at the 3- or 4-position of the phenoxy group or a -CF$_3$ group at the 3-position of the phenoxy group and $R_1$ and $R_2$ both represent hydrogen, both represent lower alkyl or one represents hydrogen and the other represents an isopropyl, sec-butyl, n-butyl, isoamyl or 2-phenylisopropyl group, and pharmaceutically acceptable acid addition salts thereof.

2. The compound according to claim 1 which is 2-hydroxy-3-(3'-chloro-phenoxy)-N-isopropyl-cyclohexylamine.

3. The compound according to claim 1 which is 2-hydroxy-3-(4'-chloro-phenoxy)-N-sec-butyl-cyclohexyalamine.

4. The compound according to claim 1 which is 2-hydroxy-3-(4'-chloro-phenoxy)-N-iso-amyl-cyclohexylamine.

5. The compound according to claim 1 which is 2-hydroxy-3-(3'-chloro-phenoxy)-N-n-butyl- cyclohexylamine.

6. The compound according to claim 1 which is 2-hydroxy-3-phenoxy-N-(2'-phenyl-isopropyl)-cyclohexylamine.

7. The compound according to claim 1 which is 2-hydroxy-3-(4'-fluorophenoxy)-N-(2'-phenyl-isopropyl)-cyclohexylamine.

8. The compound according to claim 1 which is 2-hydroxy-3-(4'-chloro-phenoxy)-cyclohexylamine.

9. A pharmaceutical composition for use as an antidepressant-psychotonic comprising a compound according to claim 1 in an amount of 50 to 100 mg. per dose as the active ingredient together with a pharmaceutically acceptable carrier which includes lactose, the amount of said carrier being greater than the amount of said active ingredient.

10. A composition according to claim 9 in unit dosage form.

11. A pharmaceutical composition according to claim 9 wherein the carrier includes cellulose and starch.

12. A pharmaceutical composition according to claim 9 wherein the active ingredient is present in an amount of approximately 50 mg., the lactose is present in an amount of approximately 108 mg., a cellulose material is present in an amount of approximately 60 mg., starch is present in an amount of approximately 31 mg., and other materials selected from polyvinylpyrrolidine, talc and stearate are present in an amount totaling approximately 11 mg.

13. A composition according to claim 12 in unit dosage form.

* * * * *